US012582365B2

(12) United States Patent
Hed et al.

(10) Patent No.: US 12,582,365 B2
(45) Date of Patent: Mar. 24, 2026

(54) APPARATUS AND METHOD OF ENHANCING COMFORTABILITY OF MAMMOGRAM IMAGING AND PROCEDURES

(71) Applicant: HED COMPOSITES, LLC., Roseville, MN (US)

(72) Inventors: Anne Hed, North Oaks, MN (US); Rebecca Hed, North Oaks, MN (US)

( * ) Notice: Subject to any disclaimer, the term of this patent is extended or adjusted under 35 U.S.C. 154(b) by 290 days.

(21) Appl. No.: 18/340,382

(22) Filed: Jun. 23, 2023

(65) Prior Publication Data

US 2023/0414184 A1 Dec. 28, 2023

Related U.S. Application Data

(60) Provisional application No. 63/377,132, filed on Sep. 26, 2022, provisional application No. 63/355,342, filed on Jun. 24, 2022.

(51) Int. Cl.
*A61B 6/04* (2006.01)
*G16H 10/60* (2018.01)

(52) U.S. Cl.
CPC ........... *A61B 6/0435* (2013.01); *G16H 10/60* (2018.01)

(58) Field of Classification Search
CPC ... A61B 6/0435; A61B 6/0414; A61B 6/0421; A61B 6/0485; G16H 10/60; G16H 30/20; G16H 30/40; G16H 40/67
See application file for complete search history.

(56) References Cited

U.S. PATENT DOCUMENTS

| | | | | |
|---|---|---|---|---|
| 5,564,438 A | * | 10/1996 | Merchant | A61N 5/10 |
| | | | | 5/613 |
| 6,974,255 B1 | * | 12/2005 | Hixson, Sr. | A61B 6/0414 |
| | | | | 378/208 |
| 9,226,718 B1 | * | 1/2016 | Baxley | A61B 6/0407 |
| 10,736,768 B2 | * | 8/2020 | Vogele | A61F 5/37 |
| 11,759,153 B2 | * | 9/2023 | DeFreitas | A61B 6/502 |
| | | | | 378/37 |
| 2007/0121782 A1 | * | 5/2007 | Sendai | A61B 6/542 |
| | | | | 378/37 |
| 2012/0114095 A1 | * | 5/2012 | Smith | A61B 6/463 |
| | | | | 378/20 |
| 2015/0282770 A1 | * | 10/2015 | Klanian | A61B 6/0414 |
| | | | | 378/208 |

(Continued)

FOREIGN PATENT DOCUMENTS

| | | | | |
|---|---|---|---|---|
| CA | 3040862 A1 | * | 5/2018 | A61B 6/0414 |

*Primary Examiner* — David J Makiya
*Assistant Examiner* — Soorena Kefayati
(74) *Attorney, Agent, or Firm* — Mueting Raasch Group

(57) ABSTRACT

A breast rest for a mammography device includes a front panel on a patient-facing side of the breast rest and a top panel having a concavity configured to accommodate a breast of a patient. A transition from the front panel to the top panel can be curved. The breast rest can be included in the mammography device. The breast rest can further include side panels. The breast rest can further include an open end to receive a breast test instrument. Multiple sizes and/or shapes of the breast rest can be provided and selected from based on patient data. Breast rests can be manufactured for particular patients having sizes and/or shapes determined from patient data.

19 Claims, 13 Drawing Sheets

(56) References Cited

U.S. PATENT DOCUMENTS

| | | | |
|---|---|---|---|
| 2016/0029979 A1* | 2/2016 | Mawdsley | A61B 6/502 |
| | | | 378/207 |
| 2016/0206229 A1* | 7/2016 | Arai | A61B 5/1075 |
| 2019/0328347 A1* | 10/2019 | Horiuchi | A61B 6/0414 |
| 2020/0060633 A1* | 2/2020 | Radicke | A61B 6/0414 |
| 2020/0069274 A1* | 3/2020 | Stango | A61B 6/5252 |
| 2020/0359975 A1* | 11/2020 | Banks | A61B 6/502 |
| 2021/0113163 A1* | 4/2021 | St. Pierre | A61B 6/502 |
| 2021/0113169 A1* | 4/2021 | Stango | A61B 6/5252 |
| 2021/0145375 A1* | 5/2021 | Defreitas | F16M 13/00 |
| 2021/0153824 A1* | 5/2021 | Koehler | A61B 6/4291 |
| 2022/0047232 A1* | 2/2022 | He | A61B 6/502 |
| 2024/0016467 A1* | 1/2024 | Ru | A61B 6/502 |

* cited by examiner

200

APPARATUS AND METHOD OF ENHANCING COMFORTABILITY OF MAMMOGRAM IMAGING AND PROCEDURES

TECHNICAL FIELD

This patent application is related to mammogram imaging and procedures. More particularly, this application describes apparatuses and methods of enhancing comfortability of the patient during mammogram imaging procedures, taking into consideration natural breast shape.

BACKGROUND

Mammograms have become one of the most important procedures that doctors or other preventive healthcare providers recommend for women in screening breast cancers. Early detection of breast cancer can significantly improve outcomes.

However, many patients dislike or even avoid mammograms because mammogram imaging and procedures are uncomfortable or even very painful. Mammogram imaging and procedures involve screening breast by placing a breast onto a breast rest plate. Traditionally, the breast rest plate is a flat surface and includes sharp edges that irritate the breasts and surrounding areas, such as the rib cage. Mammogram imaging and procedures can take up to 20+ minutes which prolong a patient's pain or causing movement by a patient in easing the pain and/or irritation.

Therefore, there is a need to improve mammogram imaging and procedures to reduce or even eliminate the pain and/or irritations.

SUMMARY

Embodiments described herein provide an improved breast rest apparatus with enhanced comfortability. In one embodiment, a breast rest apparatus is configured to include a top panel having a gradual concave shape, a side panel having a gradual concave shape, and a transition having a gradual curve connecting the top panel and the side panel, whereby a natural breast is capable of laying on the top panel while the side panel comfortably leans against a bottom portion of the natural breast and surrounding area, such as a rib cage, during mammogram imaging and procedures.

By providing surfaces having concave shapes to interface with the patient including at the rib cage and breasts, the patient can be positioned for mammogram imaging procedures without having to contact sharp edges, un-ergonomic flat surfaces, or the like. Instead, by accommodating parts of the patient in corresponding concavities joined by a smooth transition in a breast rest apparatus, patient comfort can be increased significantly compared to standard mammography machines. In turn, patients are more willing to undergo mammography, increasing the population undergoing such procedures and/or increasing the frequency of such screenings, this allowing for early detection of more breast cancers and improving the outcomes for treatment of such earlier-detected breast cancers.

Additionally, the parameters defining the concavities improving the comfort of such breast rests can be customized, to further improve patient comfort and provide comfortable breast rests across a variety of patient sizes, shapes, and conditions. The customizability can include providing a variety of different sizes and shapes. The selection among different sizes and shapes can be further improved based on the use of patient data to match patients to particular sizes and shapes of breast rests. In an embodiment, the breast rests can have sizes and shapes that are custom to a particular patient. The custom breast rests can be based on patient data, and optionally produced by way of three-dimensional printing to provide a fully customized breast rest to further improve comfort during mammography.

In an embodiment, a breast rest apparatus includes a top panel and a front panel. The top panel and the front panel are connected by a curved transition. The top panel includes a first concavity, and the front panel includes a second concavity.

In an embodiment, the breast rest apparatus further includes a first side panel. In an embodiment, the first side panel and the top panel are joined by a second curved transition. In an embodiment, the breast rest apparatus further includes a second side panel. In an embodiment, the first side panel and the top panel are joined by a second curved transition.

In an embodiment, the breast rest apparatus includes an open end configured to receive a breast test instrument.

In an embodiment, the breast rest apparatus includes a carbon material.

In an embodiment, a shape and/or a size of the first concavity and/or a shape and/or size of the second concavity are based on patient data of a patient, wherein the patient data includes at least one of patient size data and patient treatment history.

In an embodiment, a mammogram imaging system includes a mammogram imaging device and the breast rest apparatus.

In an embodiment, a plurality of breast rest apparatuses is provided, and each of the plurality of breast rest apparatuses differs in a shape of at least one of the first concavity or the second concavity.

In an embodiment, a system includes a plurality of breast rest apparatuses and a processor configured to receive patient data of a patient and determine one of the plurality of breast rest apparatuses for use with the patient, wherein the patient data includes at least one of patient size data and patient treatment history. In an embodiment, the system further includes a mammogram imaging device.

In an embodiment, a system for producing a breast rest apparatus includes a processor and a three-dimensional printer. The processor is configured to receive patient data of a patient. The patient data includes at least one of patient size data and patient treatment history. The processor is further configured to determine a configuration for a breast rest apparatus based on the patient data. The configuration of the breast rest apparatus includes a shape of at least one of a first concavity provided on a top panel or a second concavity provided on a front panel. The three-dimensional printer is configured to produce the breast rest apparatus according to the determined configuration. The breast rest apparatus includes the top panel and the front panel, and the top panel and the front panel are connected by a curved transition.

In an embodiment, the breast rest apparatus further comprises an open end configured to receive a breast test instrument. In an embodiment, a mammography imaging system includes the system for producing the breast rest apparatus, and a mammogram imaging device configured to use the breast rest apparatus.

A more complete understanding of the embodiments and the advantages thereof may be appreciated by the following description and drawings.

DETAILED DESCRIPTION

Figure 1:
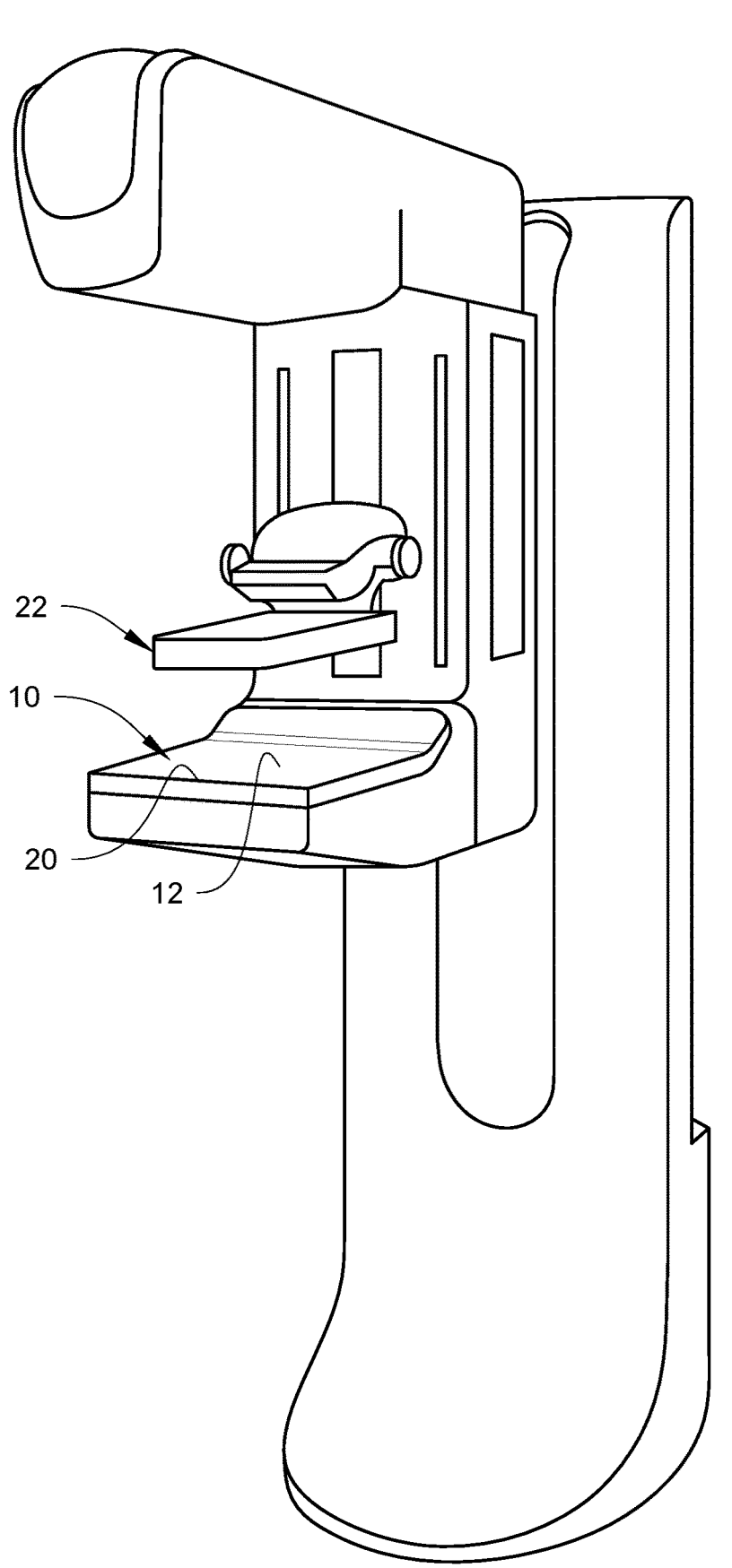
FIG. 1 is a prior art mammogram imaging system having a flat surface and sharp edges for breast rest.
Figure 2:
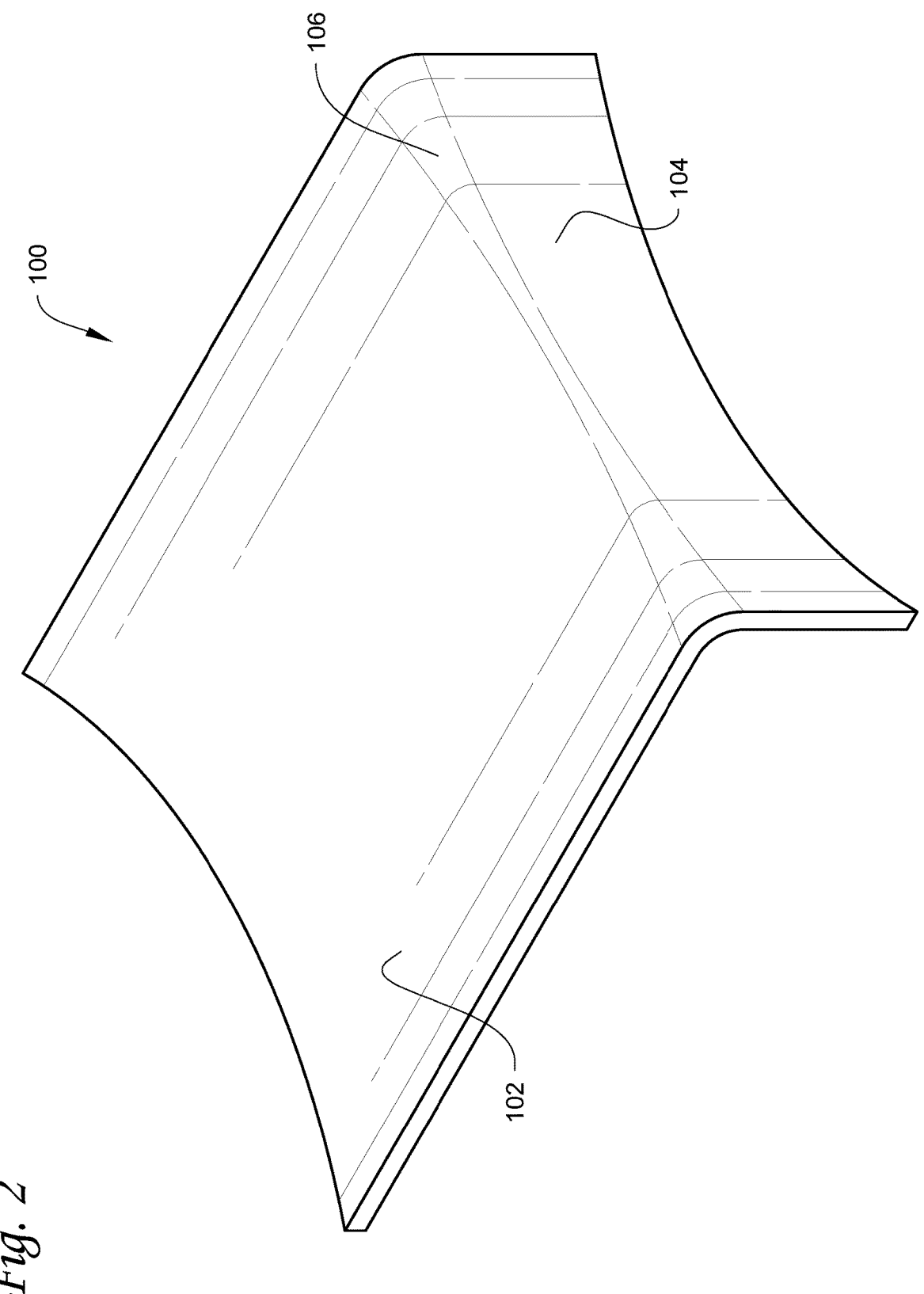
FIG. 2 is an isometric view of a breast rest apparatus according to an embodiment.
Figure 3:
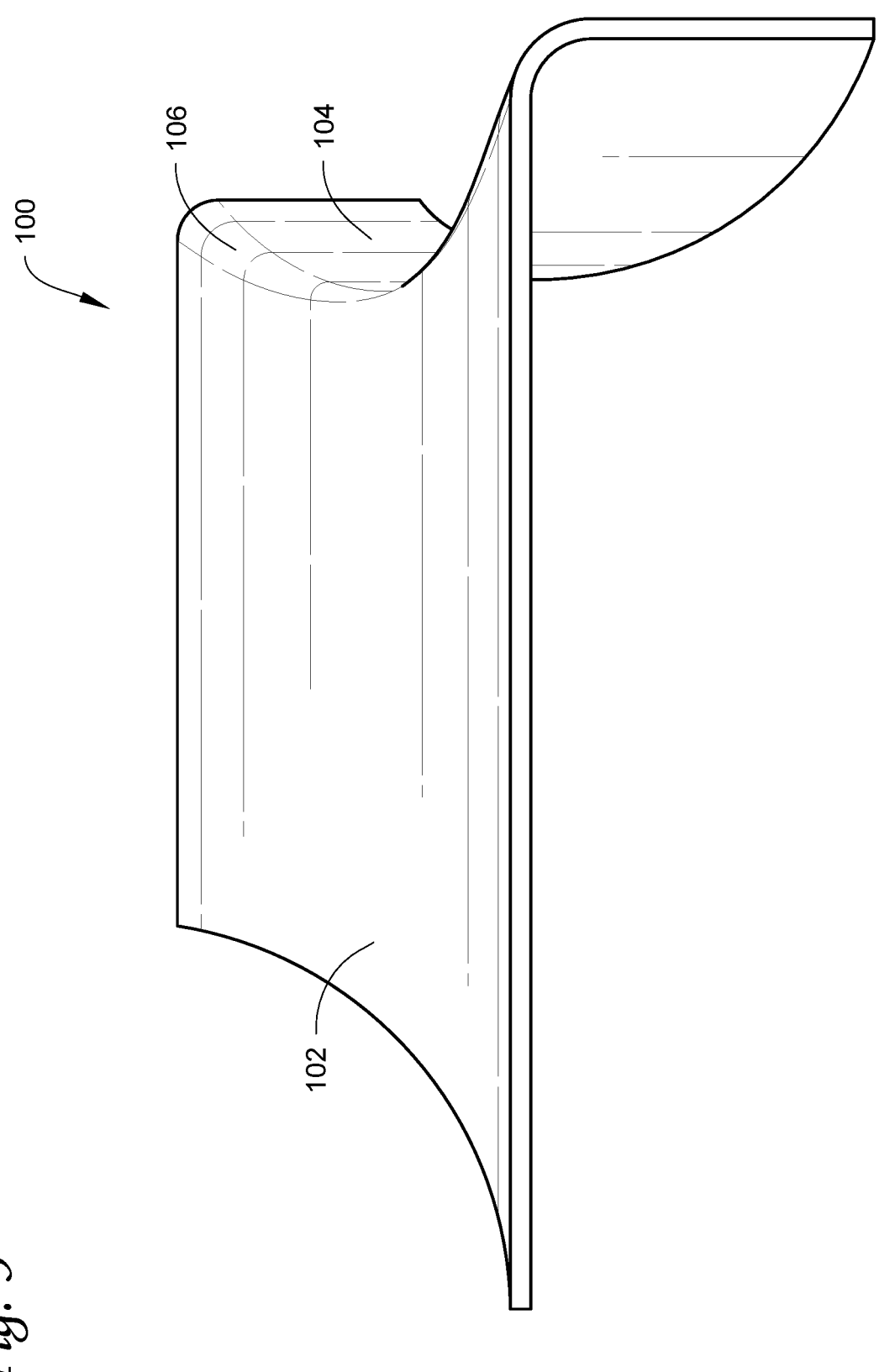
FIG. 3 is a left side view of a breast rest apparatus of FIG. 2.
Figure 4:
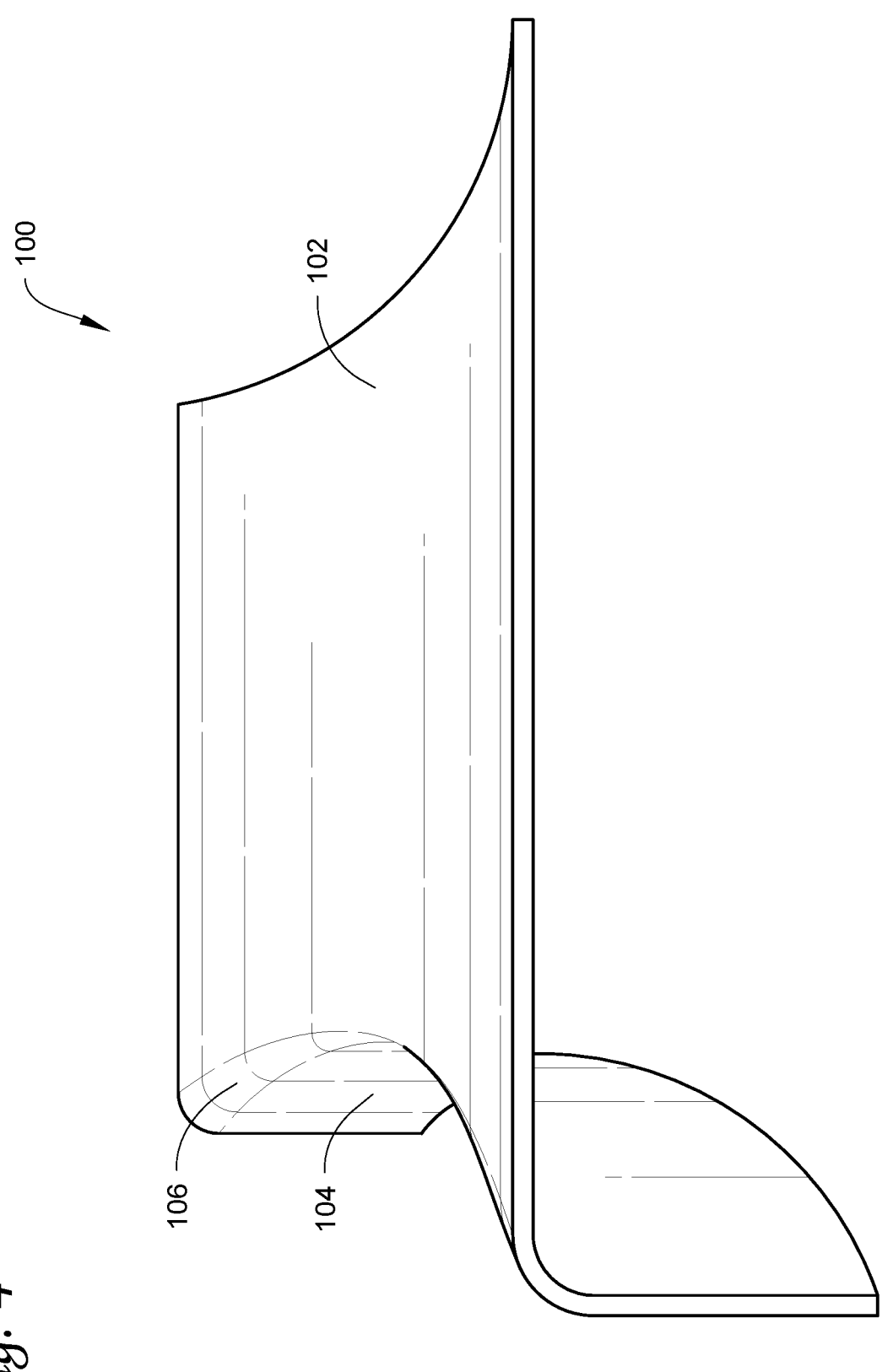
FIG. 4 is a right side view of the breast rest apparatus of FIG. 2.
Figure 5:
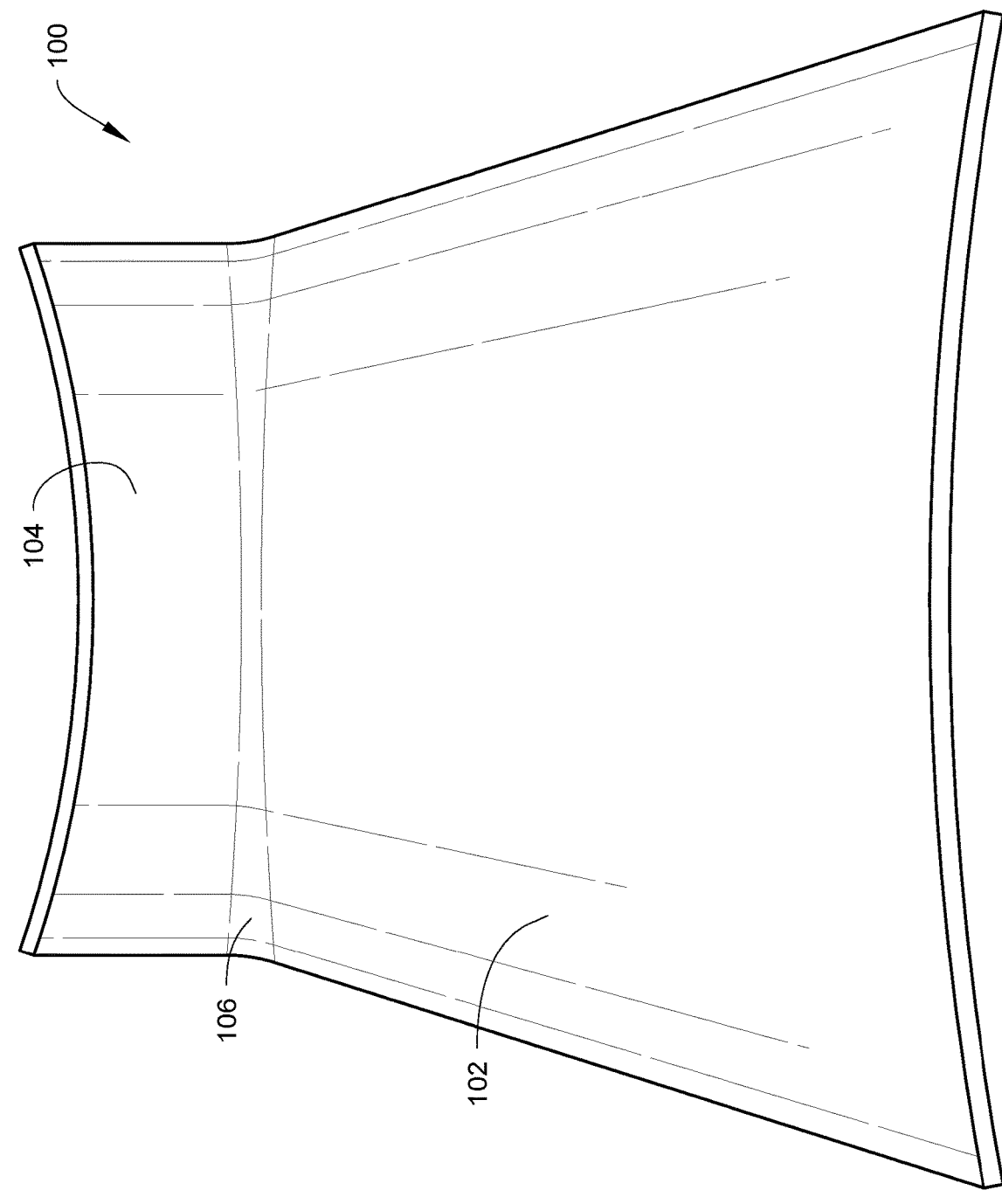
FIG. 5 is a bottom rear perspective view of the breast rest apparatus of FIG. 2.
Figure 6:
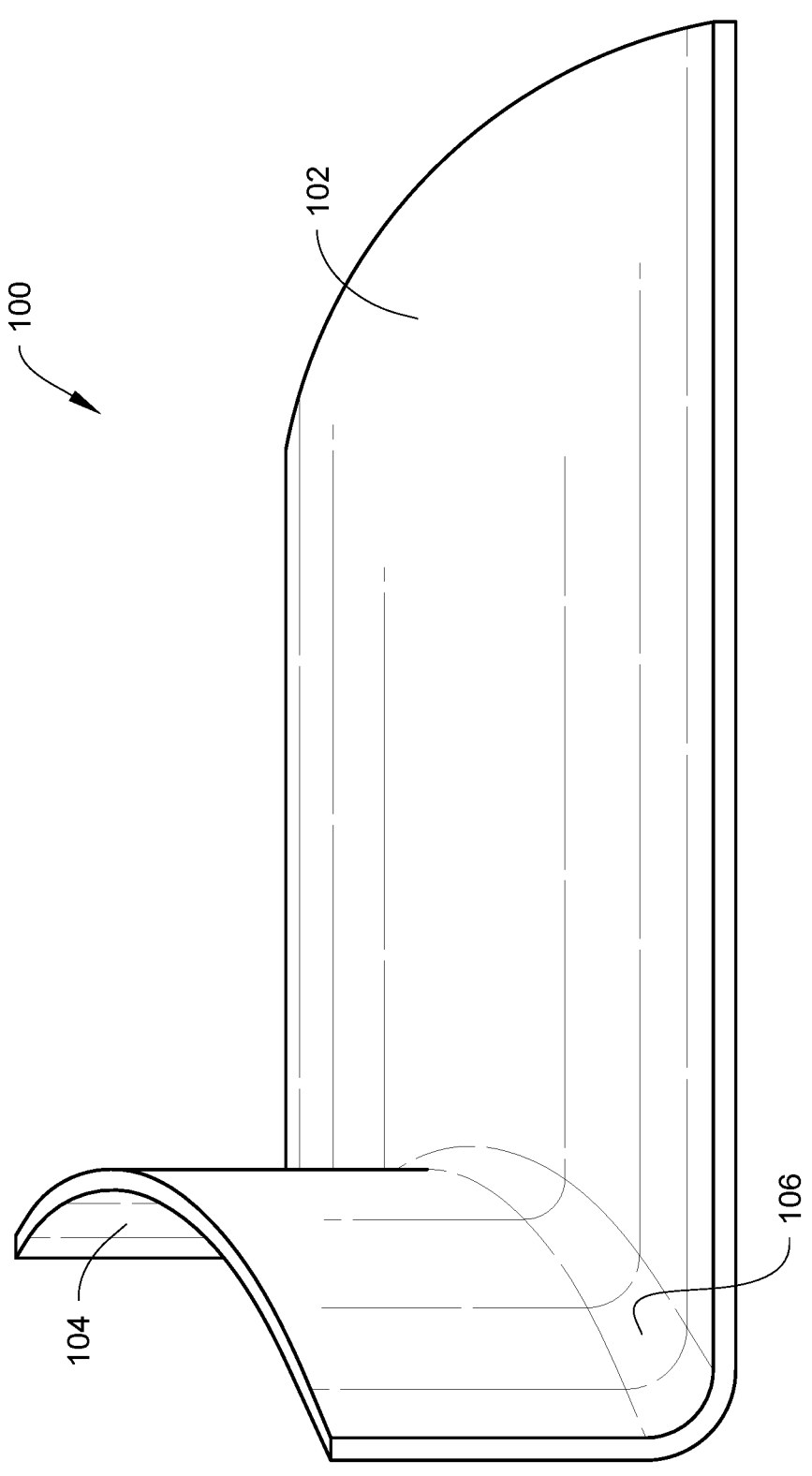
FIG. 6 is a side view of the bottom of the breast rest apparatus of FIG. 2.
Figure 7:
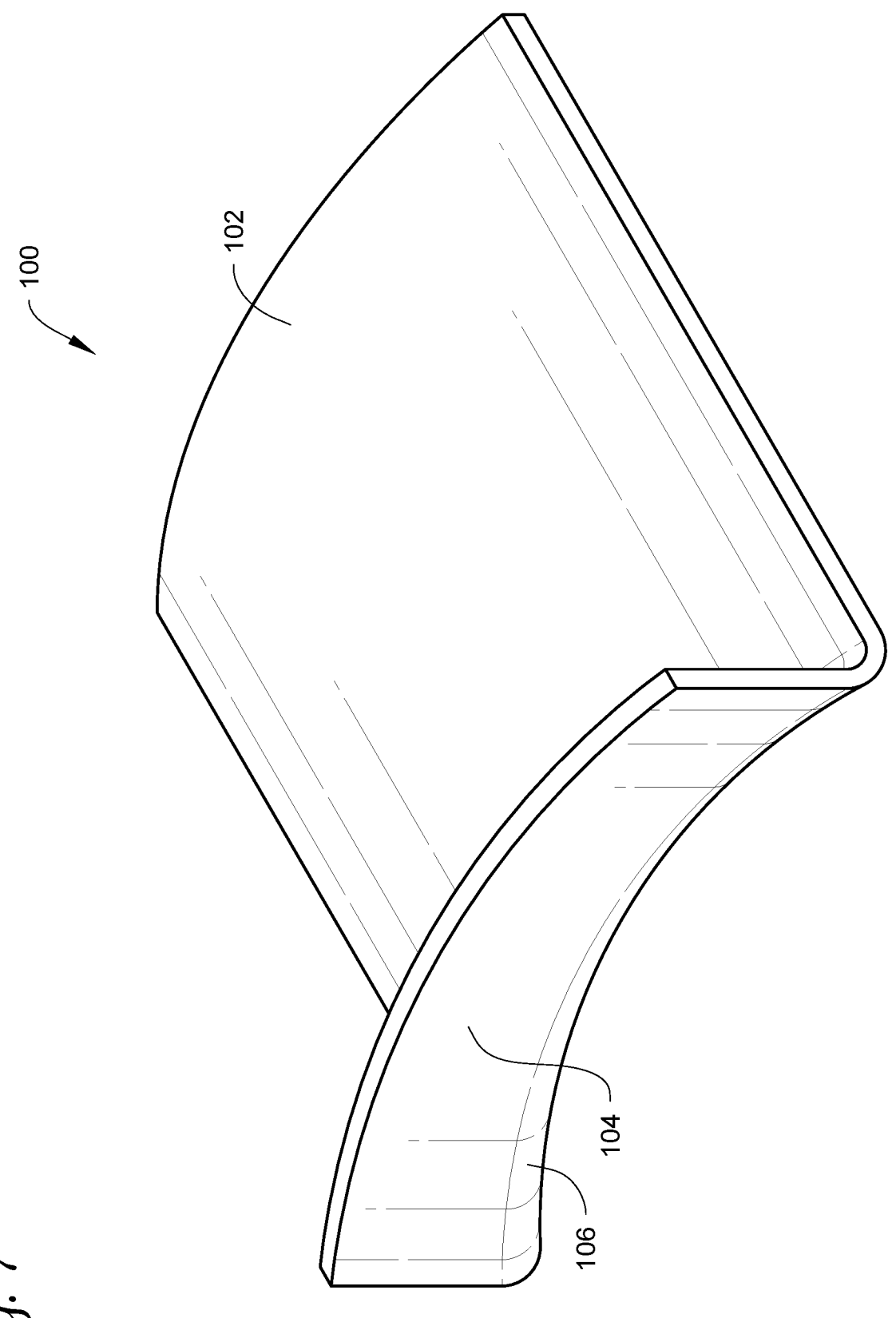
FIG. 7 is an isometric view of a bottom of the breast rest apparatus of FIG. 2.
Figure 8:
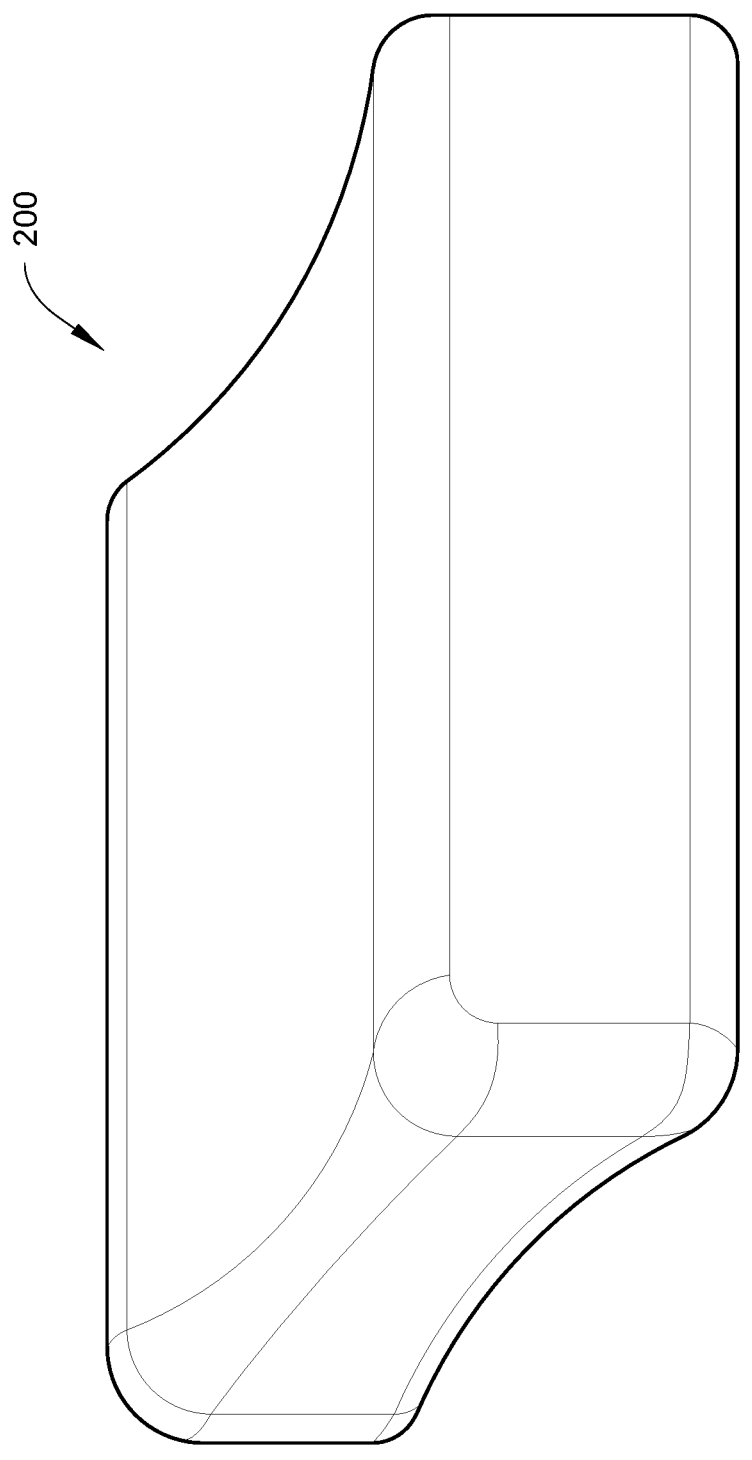
FIG. 8 is an isometric view of one embodiment of a breast rest apparatus.

In FIG. 1, a traditional mammogram imaging system according to the prior art is shown, having a breast rest plate 10 and a pressing plate 22. The breast rest plate 10 has a flat surface 12 and shape edges 20. In a mammogram imaging procedure, a patient breast is placed on top of the flat surface 12. During the mammogram imaging procedure, the breast and its surrounding area such as the rib cage are forced against the sharp edges 20 of the flat surface 12 of the breast rest plate 10 while the pressing plate 22 is being pressed onto the breast for imaging. The sharp edges of the breast rest plate 10 irritate the breast and the surrounding area.

An embodiment of the improved breast rest apparatus 100 is shown in FIGS. 2-7. The breast rest apparatus 100 is configured to include a top panel 102, a front panel 104, and a transition 106 connecting the top panel 102 and the front panel 104.

Top panel 102 forms an upper surface of breast rest apparatus 100 when the breast rest apparatus 100 is provided on a mammogram imaging machine. The top panel 102 includes a concavity. In an embodiment, the concavity provided in top panel 102 can be a continuous concavity defined across a width of top panel 102 from a left side to a right side of top panel 102. In an embodiment, the concavity provided in top panel 102 can be provided along an entire length of the top panel 102. In an embodiment, the concavity is provided in top panel 102 in only a certain region of the top panel 102 which may be contacted by a natural breast during a mammogram imaging procedure. The concavity can be shaped and sized to accommodate the breasts of the patient when the breasts are laying on the top panel 102, so as to improve comfort of the patient during the mammogram imaging procedure. In embodiments, the size and/or shape of the concavity can be determined based on patient data as discussed below.

Front panel 104 is provided at a front of the breast rest apparatus 100, such that the front panel 104 faces the patient when the patient is using breast rest apparatus 100 during a mammogram imaging procedure. Front panel 104 includes a concavity, extending inwards away from the patient when the patient is using breast rest apparatus 100 during a mammogram imaging procedure. In an embodiment, the concavity provided in front panel 104 can be a continuous concavity defined across a width of front panel 104 from a left side to a right side of front panel 104. In an embodiment, the concavity provided in front panel 104 can be defined across a portion of the width of front panel 104. The concavity can be shaped and sized to contact a bottom portion of the patient's breast and surrounding areas, such as a rib cage of the patient, during the mammogram imaging and procedures. In embodiments, the size and/or shape of the concavity can be determined based on patient data as discussed below.

Transition 106 connects front panel 104 to top panel 102. The transition 106 is a curved surface, for example being radiused or otherwise smoothed, to provide a continuous surface without sharp edges where front panel 104 meets top panel 102 in breast rest apparatus 100. The transition 106 can include continuations of the concavities provided in one or both of front panel 104 and top panel 102. Transition 106 can further improve comfort by avoiding the presence of sharp edges that may contact the patient at the ribs, under or on a bottom portion of the breasts, or the like. In embodiments, the size and/or shape of the transition 106 can be determined based on patient data as discussed below.

In an embodiment, the breast rest apparatus 100 is a detachable element configured to be attached to or removed from a mammogram imaging system such as the mammogram imaging system shown in FIG. 1. In an embodiment, the breast rest apparatus is provided integrally with a mammogram imaging system such as the mammogram imaging system shown in FIG. 1, for example in place of breast rest plate 10 as shown in FIG. 1.

In an embodiment, the breast rest apparatus 100 can be formed of any suitable material. Suitable materials for breast rest apparatus 100 can be selected based on requirements for mammography measurement, such as rigidity, ability to support the breast during imaging, potential to interfere with measurements (such as effects on radiation used in the mammography), and the like. In embodiments, suitability of materials can further include factors for patient comfort such as surface texture, heat transfer properties, and the like. Non-limiting examples of suitable materials include carbon materials, such as carbon fiber structures, carbon fiber composites, moldable carbon materials, and the like.

In an embodiment, a plurality of breast rest apparatuses 100 can be provided having various contours for the concavities provided in the top and front panels 102, 104 and the transition 106 can be molded to fit various different sizes, shapes, or other features of the breasts of patients.

Another embodiment of a breast rest apparatus 200 is shown in FIGS. 8-13. The breast rest apparatus 200 is configured to include a top panel 202, a right side panel 204, a front panel 206, and a transition 208 connecting front panel 206 and top panel 202.

Top panel 202 forms an upper surface of breast rest apparatus 200 when the breast rest apparatus 200 is provided on a mammogram imaging machine. The top panel 202 includes a concavity. In an embodiment, the concavity provided in top panel 202 can be a continuous concavity defined across a width of top panel 202 from a left side to a right side of top panel 202. In an embodiment, the concavity provided in top panel 202 can be provided along an entire length of the top panel 202. In an embodiment, the concavity is provided in top panel 202 in only a certain region of the top panel 202 which may be contacted by a natural breast during a mammogram imaging procedure. The concavity can be shaped and sized to accommodate the breasts of the patient when the breasts are laying on the top panel 202, so as to improve comfort of the patient during the mammogram imaging procedure. In embodiments, the size and/or shape of the concavity can be determined based on patient data as discussed below.

Right side panel 204 is a panel provided on a right side of the breast rest apparatus 200, such that the right side panel 204 is to the right side of a patient when the patient is using the breast rest apparatus 200 during a mammogram imaging procedure. In an embodiment, the right side panel 204 can is a straight panel, with no concavity or convexity outside of transition 208. In an embodiment, the right side panel 204 can include concavity or convexity. In an embodiment, the right side panel 204 can include rounding, radiusing, or other smoothing along a bottom portion of the right side panel 204.

Front panel 206 is provided at a front of the breast rest apparatus 200, such that the front panel 206 faces the patient when the patient is using breast rest apparatus 200 during a mammogram imaging procedure. Front panel 206 includes a concavity, extending inwards away from the patient when the patient is using breast rest apparatus 200 during a mammogram imaging procedure. In an embodiment, the concavity provided in front panel 206 can be a continuous concavity defined across a width of front panel 206 from a left side to a right side of front panel 206. In an embodiment, the concavity provided in front panel 206 can be defined across a portion of the width of front panel 206. The concavity can be shaped and sized to contact a bottom portion of the patient's breast and surrounding areas, such as a rib cage of the patient, during the mammogram imaging and procedures. In embodiments, the size and/or shape of the concavity can be determined based on patient data as discussed below.

Transition 208 connects right side panel 204 and front panel 206 to top panel 202. The transition 208 is a curved surface, for example being radiused or otherwise smoothed, to provide a continuous surface without sharp edges where right side panel 204 and front panel 206 meet top panel 202 in breast rest apparatus 200. The transition 208 can include continuations of the concavities provided in one or both of front panel 206 and top panel 202. Transition 208 can further improve comfort by avoiding the presence of sharp edges that may contact the patient at the ribs, under or on a bottom portion of the breasts, or the like. In embodiments, the size and/or shape of the transition 208 can be determined based on patient data as discussed below. Transition 208 can further extend continuously along where right side panel 204 connects to top panel 202, with radiusing, formation of a rounded corner, or other smoothing as transition 208 turns from extending along front panel 206 to extending along right side panel 204. In an embodiment, transition 208 can include discrete curved transitions at each of the connection of right side panel 204 to top panel 202 and front panel 206 to top panel 202.

Figure 10:
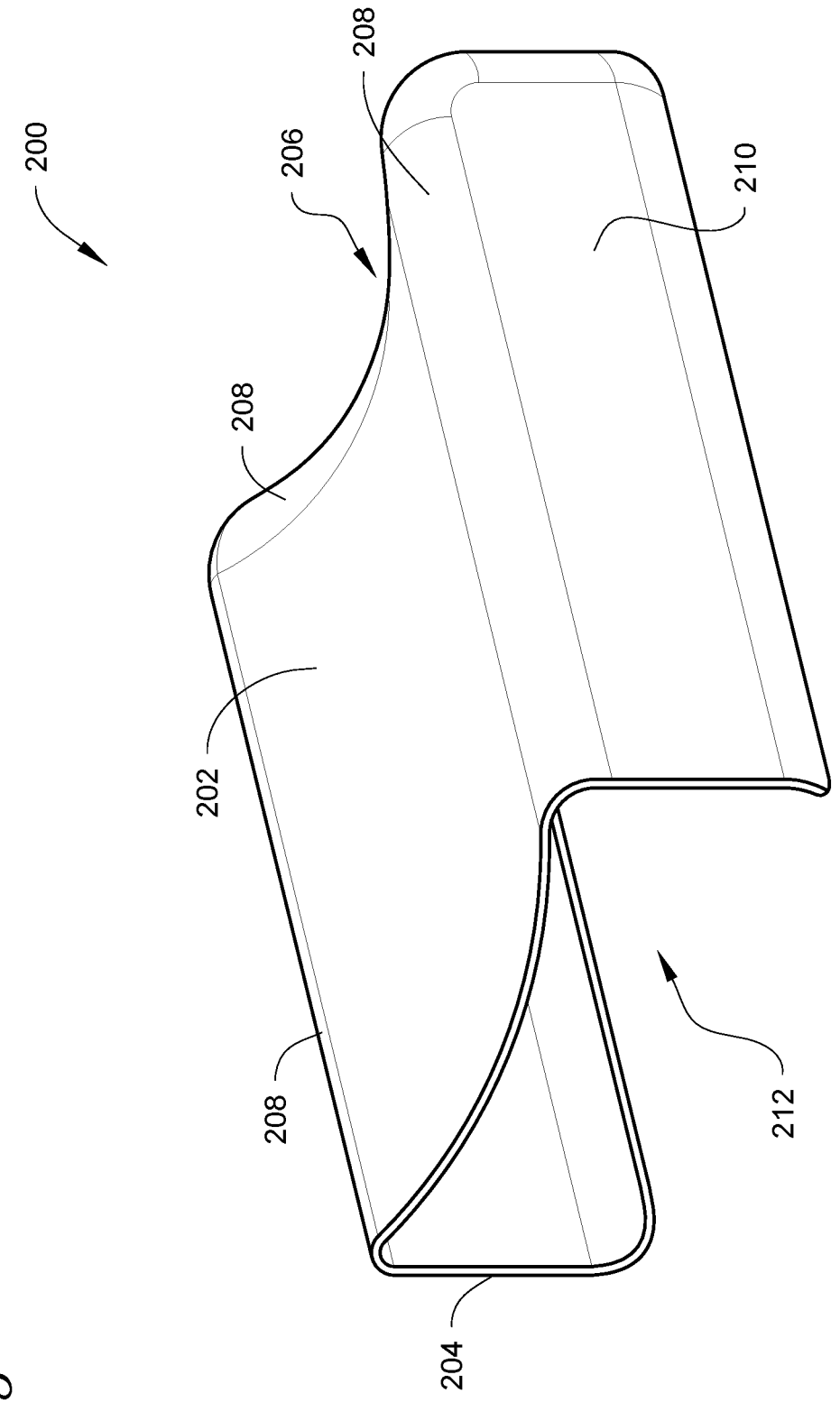
FIG. 10 is another perspective view of the embodiment of the breast rest apparatus shown in FIG. 8 showing top, rear, and left side views.
Figures 11, 12:
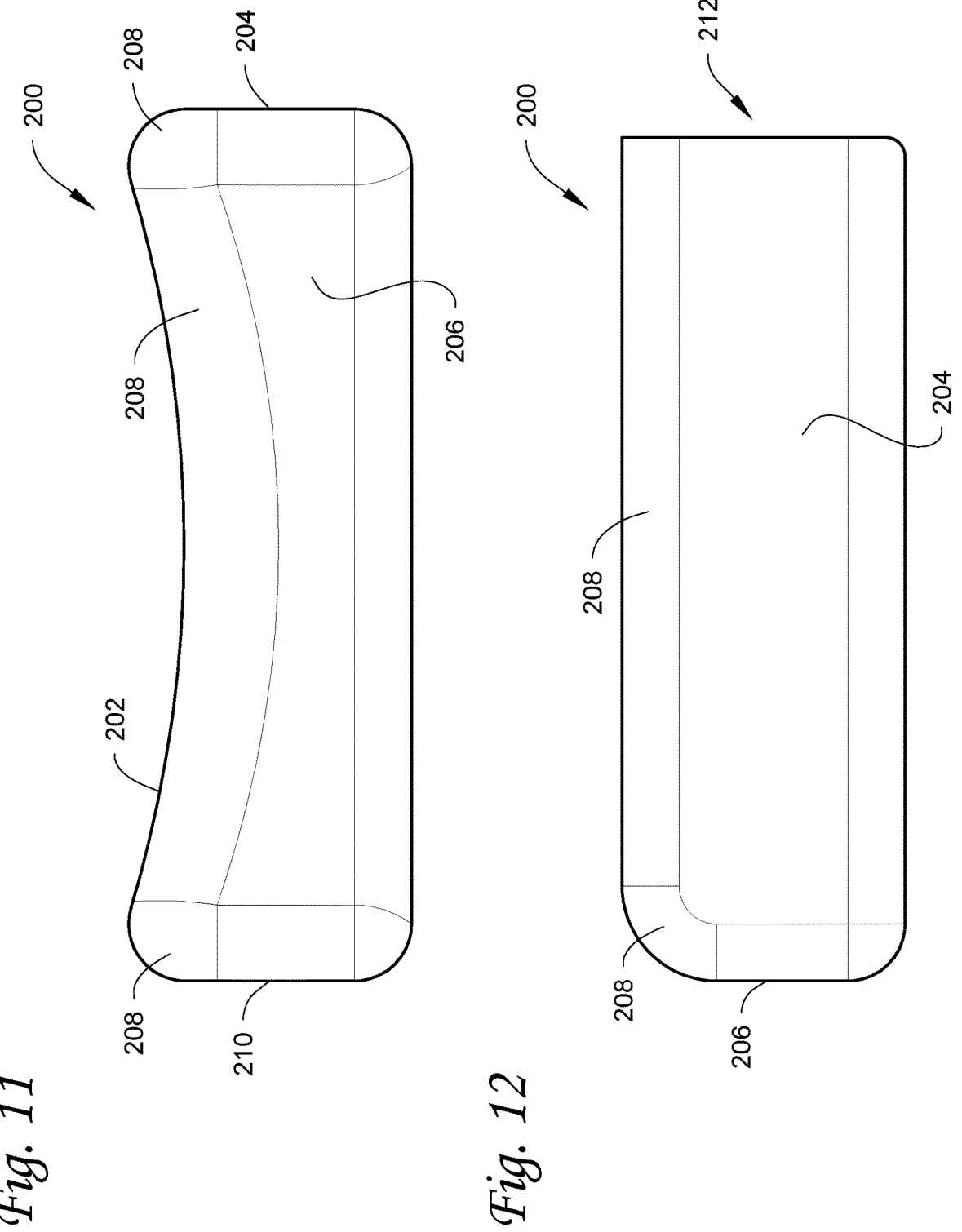
FIG. 11 is an elevated front view of the embodiment of the breast rest apparatus shown in FIG. 8.
FIG. 12 is an elevated right side view of the embodiment of the breast rest apparatus shown in FIG. 8.

In an embodiment of breast rest apparatus 200, a left side panel 210 is molded in a mirror image of the right side panel 204 as shown in FIGS. 10-11, including a concavity corresponding to a mirror image of the concavity provided in right side panel 204. In an embodiment, the transition 208 or a portion thereof connects the left side panel 210 and the top panel 202. In an embodiment, the connection of left side panel 210 to the top panel 202 can be a continuation of transition 208, with, for example, radiusing, a rounded corner, or the like where transition 208 turns from extending along front panel 206 to extending along left side panel 210. In an embodiment, a discrete portion of transition 208 is provided at the connection of the left side panel 210 and the top panel 202.

Figure 9:
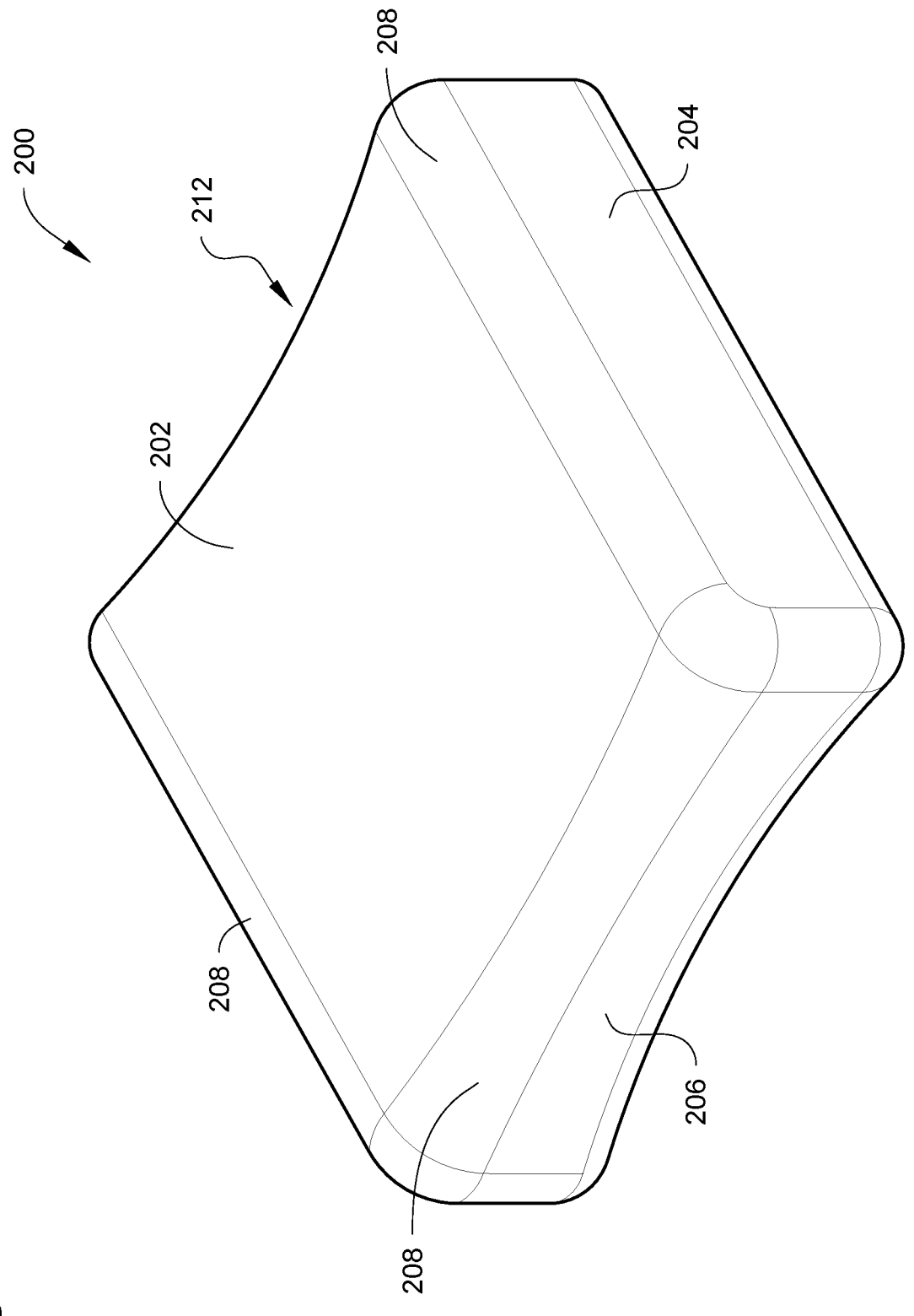
FIG. 9 is a perspective view of one embodiment of the breast rest apparatus shown in FIG. 8 showing top, front, and right side views.
Figure 13:
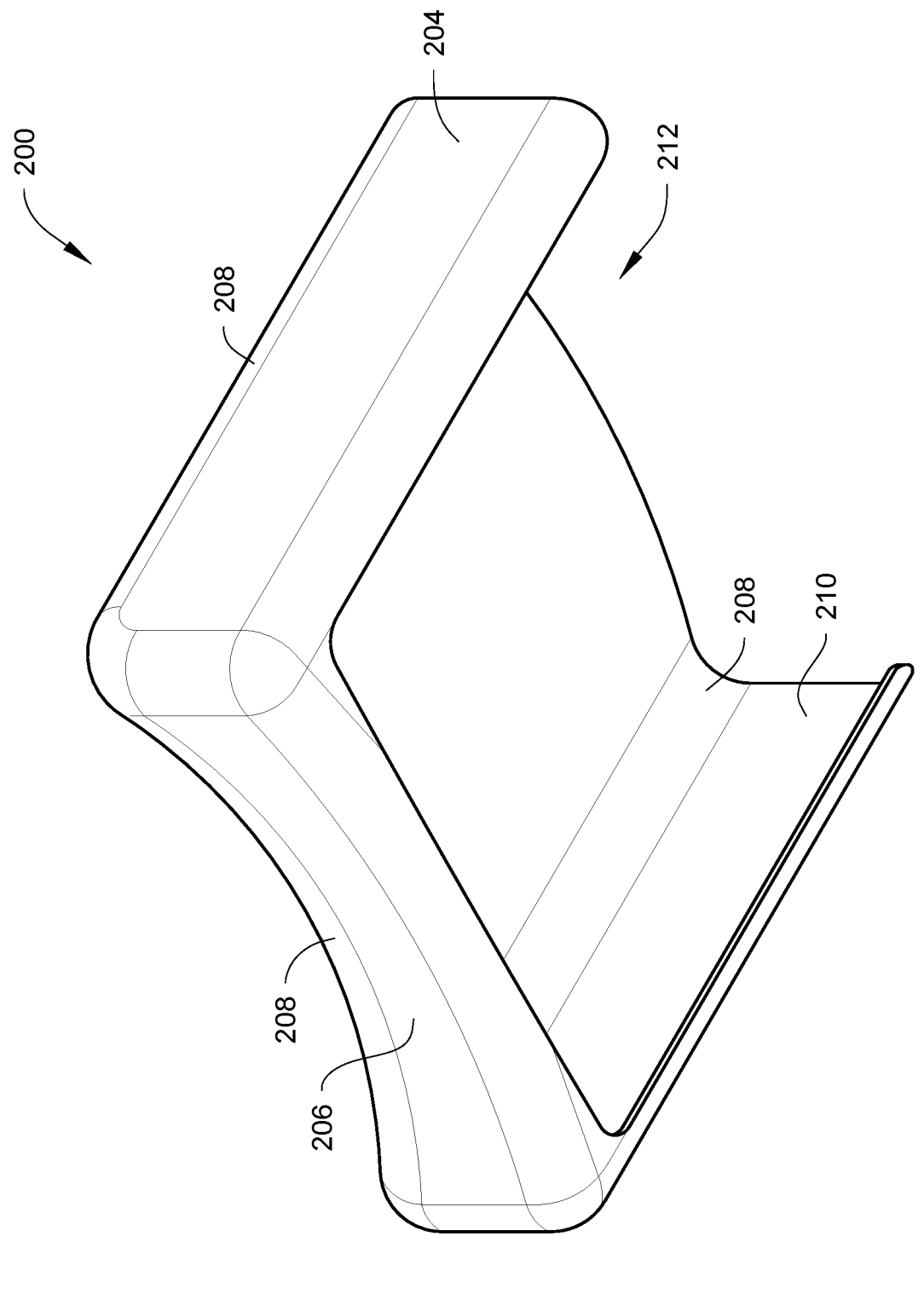
FIG. 13 is a yet another perspective view of the embodiment of the breast rest apparatus shown in FIG. 8 showing bottom, front, and right side views.

In an embodiment, breast rest apparatus includes open end 212, as can be seen in FIGS. 9, 12, and 13. Open end 212 can be a recess, depression, or opening formed in the body of breast rest apparatus 200 that is configured to receive a breast test instrument, for example a part of the mammogram imaging system shown in FIG. 1. Open end 212 can include an absence of a wall on a rear side of the breast rest apparatus 200, for example having no panel opposing the front panel 206. The open end 212 can have any suitable size and shape for receiving the breast test instrument that breast rest apparatus 200 is configured for use with. For example, open end 212 can be configured such that open end 212 can form a press-fit with a corresponding breast test instrument or otherwise provide a shape suitable for use with a corresponding breast test instrument.

In an embodiment, the breast rest apparatus 200 is a detachable element configured to be attached to or removed from a mammogram imaging system such as the mammogram imaging system shown in FIG. 1. In an embodiment, the breast rest apparatus is provided integrally with a mammogram imaging system such as the mammogram imaging system shown in FIG. 1, for example in place of breast rest plate 10 as shown in FIG. 1.

In an embodiment, the breast rest apparatus 200 can be formed of any suitable material. Suitable materials for breast rest apparatus 200 can be selected based on requirements for mammography measurement, such as rigidity, ability to support the breast during imaging, potential to interfere with measurements (such as effects on radiation used in the mammography), and the like. In embodiments, suitability of materials can further include factors for patient comfort such as surface texture, heat transfer properties, and the like. Non-limiting examples of suitable materials include carbon materials, such as carbon fiber structures, carbon fiber composites, moldable carbon materials, and the like.

In an embodiment, a plurality of breast rest apparatuses 200 can be provided having various contours for the concavities provided in the top, side, and front panels 202, 204, 210, 206, and the transition 208 can be molded to fit various different sizes, shapes, or other features of the breasts of patients.

Figure 14:
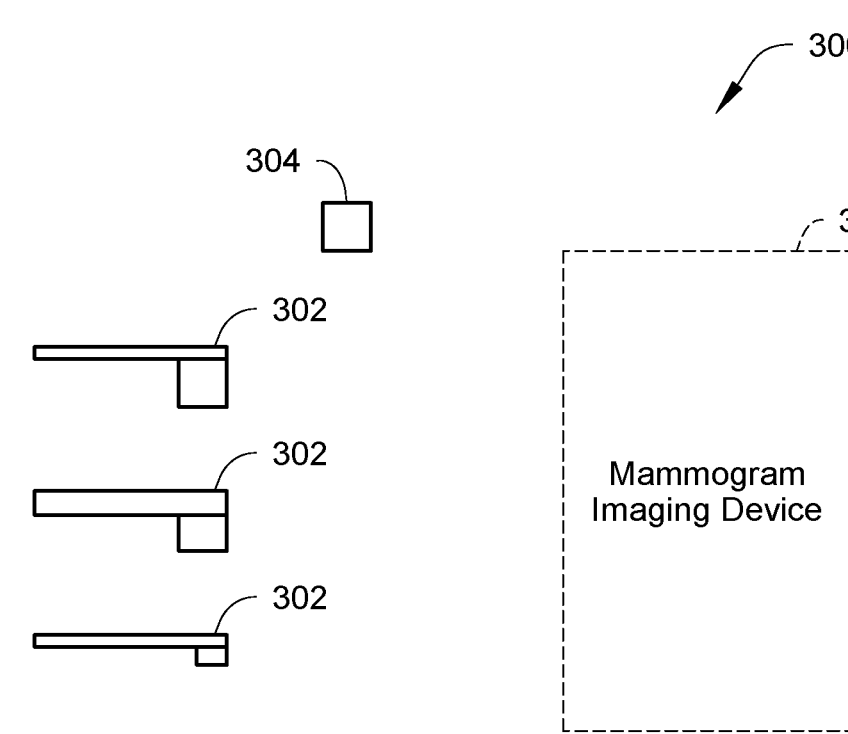
FIG. 14 is a system diagram of a system for mammogram imaging according to an embodiment.

FIG. 14 is a system diagram of a system for mammogram imaging according to an embodiment. System 300 includes a plurality of breast rests 302, a processor 304, and optionally a mammogram imaging device 306.

Breast rests 302 are a plurality of breast rests such as breast rest apparatus 100 or breast rest apparatus 200. The breast rests 302 have varying sizes and shapes of the concavities and transitions provided therein, such that the breast rests 302 are suited to different sizes, shapes, and/or other conditions of patients.

Processor 304 is configured to receive patient data for a patient that is to receive a mammogram. The patient data can include, for example, patient height, patient weight, patient medical history data such as the patient's treatment history, past procedures on the breasts, past mammogram results, and the like, patient breast size data such as band or cup sizes, historical patient comfort data such as survey data or health provider notes, and the like. The patient data can then be processed using the processor 304 to determine one breast rest of the plurality of breast rests 302 that is most suited to the patient. The processing of the patient data can be performed using, for example, one or more algorithms, machine learning models, artificial intelligence (AI) models, combinations thereof, and the like. The processor 304 can be provided on any suitable device, such as a cloud server, a local computing device such as a laptop, desktop, local server, or the like, or a mobile device, for example a tablet, smartphone, or the like.

Mammogram imaging device 306 can optionally be included in the system. The mammogram imaging device 306 can be the mammogram imaging device shown in FIG. 1, except allowing for the use of one of the breast rests 302 in place of the breast rest plate 10 described above and shown in FIG. 1. The mammogram imaging device 306 can be configured such that the breast rests 302 can be attached or removed such that the breast rest selected by processor 304 can be used when a particular patient is having a mammogram on the mammogram imaging device 306.

Figure 15:
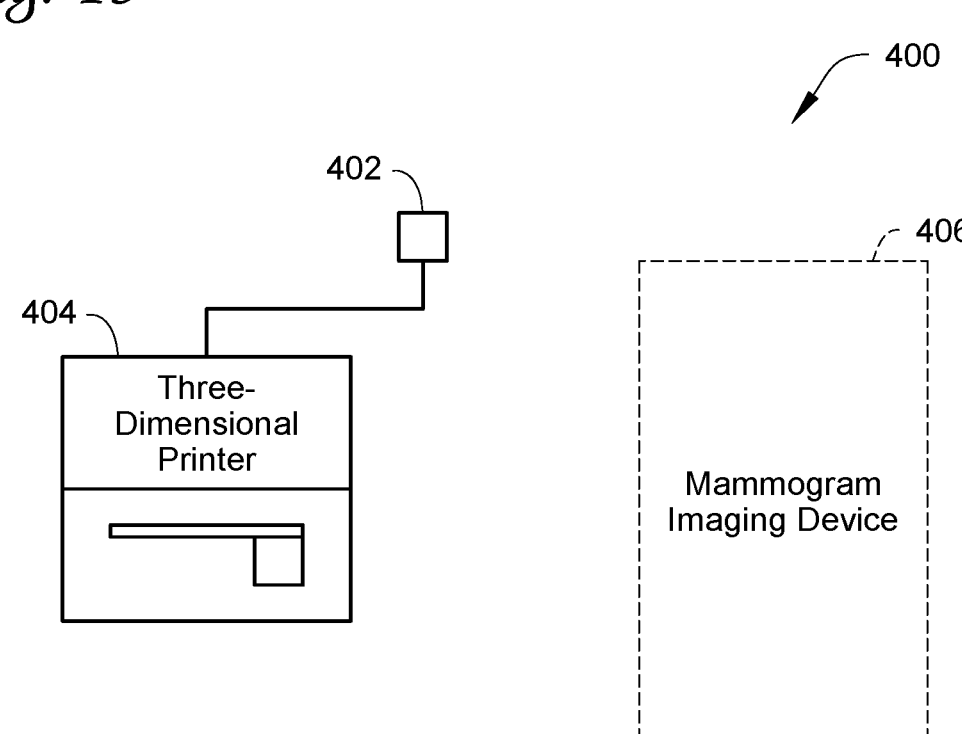
FIG. 15 is a system diagram of a system for producing a breast rest according to an embodiment.

FIG. 15 is a system diagram of a system for producing a breast rest according to an embodiment. System 400 includes processor 402, three-dimensional printer 404, and optionally mammogram imaging device 406.

Processor 402 is configured to receive patient data for a patient to receive a mammogram. The patient data can include, for example, patient height, patient weight, patient medical history data such as the patient's treatment history, past procedures on the breasts, past mammogram results, and the like, patient breast size data such as band or cup sizes, historical patient comfort data such as survey data or health provider notes, and the like. The patient data can then be processed using the processor 402 to determine a configuration of a breast rest specific to the patient. The breast rest for which the configuration is determined by processor 402 can be any breast rest as described herein such as breast rest 100 or breast rest 200 described above and shown in FIGS. 2-7 and 8-13, respectively. The configuration of the breast rest determined by processor 402 can include one or more of a size and/or shape a concavity provided on a top panel, a size and/or shape of concavity provided on a front panel, a shape of a transition from the top panel to the front panel, a shape of a concavity provided on a left side or right side panel, a shape of a transition from the top panel and/or the front panel to one of the left side or right side panels, or any other suitable variable parameter of the breast rest. The configuration of the breast rest determined by processor 402 can include fixed values for parameters relating to operability of the resulting breast rest with mammogram imaging device 406, such as depth, width, the presence of any attachment features, and the like. The processing of the patient data can be performed using, for example, one or more algorithms, machine learning models, artificial intelligence (AI) models, combinations thereof, and the like. The processor 402 can be provided on any suitable device, such as a cloud server, a local computing device such as a laptop, desktop, local server, or the like, a mobile device, for example a tablet, smartphone, or the like, integrally with the three-dimensional printer 404, or the like.

Three-dimensional printer 404 is a printer configured to print three-dimensional structures according to the configuration determined by processor 402. Three-dimensional printer 404 can be any suitable three-dimensional printer capable of printing using a suitable material for the breast rest as defined herein and printing objects of a suitable size corresponding to the size of the breast rests. Three-dimensional printer 404 can be connected to the processor 402 through any suitable means, such as wired or wireless connections, integration of processor 402 into three-dimensional printer 404, or the like. Three-dimensional printer 404 can further include any suitable processors or other additional features to implement the printing of three-dimensional structures according to the configuration determined by processor 402.

Optional mammogram imaging device 406 can be included in system 400. The mammogram imaging device 406 can be the mammogram imaging device shown in FIG. 1, except allowing for the use of one of the breast rests produced by three-dimensional printer 404 according to the configuration determined by processor 402 in place of the breast rest plate 10 described above and shown in FIG. 1. The mammogram imaging device 406 can be configured such that the breast rests produced by the three-dimensional printer 404 can be attached or removed such that the breast rest produced for a particular patient can be used when said particular patient is having a mammogram on the mammogram imaging device 406.

Embodiments described herein provide an advantage of providing the same maximized mammographic images with significantly enhanced comfortability for the patient during the imaging process. Embodiments described herein provide other advantages such as providing AI adapted features for improved customization and further increases in patient comfort.

In the foregoing patent application, the disclosure has been described and shown with reference to specific embodiments. However, as one skilled in the art can appreciate, embodiments of breast rest apparatus(es) and method(s) thereof described herein can be modified or otherwise implemented in many ways without departing from the spirit and scope of the disclosure. Accordingly, this disclosure is to be construed as illustrative only and is for the purpose of teaching those skilled in the art the manner of making and using other embodiments. It is to be understood that the forms of the disclosure herein shown and described is to be taken as exemplary embodiments. Equivalent elements or materials may be substituted for those illustrated and described herein. Moreover, certain features of the disclosure may be utilized independently of the use of other features, all as would be apparent to one skilled in the art after having the benefit of this description of the disclosure.

Aspects

It is understood that any of aspects 1-11 can be combined with any of aspects 12-14.

Aspect 1. A breast rest apparatus comprising a top panel and a front panel, wherein the top panel and the front panel are connected by a curved transition, the top panel includes a first concavity, and the front panel includes a second concavity.

Aspect 2. The breast rest apparatus according to aspect 1, further comprising a first side panel.

Aspect 3. The breast rest apparatus according to aspect 2, wherein the first side panel and the top panel are joined by a second curved transition.

Aspect 4. The breast rest apparatus according to any of aspects 2-3, further comprising a second side panel.

Aspect 5. The breast rest apparatus according to aspect 4, wherein the first side panel and the top panel are joined by a second curved transition.

Aspect 6. The breast rest apparatus according to any of aspects 1-5, comprising an open end configured to receive a breast test instrument.

Aspect 7. The breast rest apparatus according to any of aspects 1-6, wherein the breast rest apparatus includes a carbon material.

Aspect 8. The breast rest apparatus of according to any of aspects 1-7, wherein a shape and/or a size of the first concavity and/or a shape and/or size of the second concavity are based on patient data of a patient, wherein the patient data includes at least one of patient size data and patient treatment history.

Aspect 9. A mammogram imaging system comprising a mammogram imaging device and the breast rest apparatus according to any of aspects 1-8.

Aspect 10. A plurality of breast rest apparatuses according to any of aspects 1-7, wherein each of the plurality of breast rest apparatuses differs in a shape of at least one of the first concavity or the second concavity.

Aspect 11. A system, comprising the plurality of breast rest apparatuses according to aspect 10 and a processor configured to receive patient data of a patient and determine one of the plurality of breast rest apparatuses for use with the patient, wherein the patient data includes at least one of patient size data and patient treatment history.

Aspect 12. The system according to aspect 11, further comprising a mammogram imaging device.

Aspect 13. A system for producing a breast rest apparatus, comprising:

a processor configured to:

receive patient data of a patient, wherein the patient data includes at least one of patient size data and patient treatment history, and determine a configuration for a breast rest apparatus based on the patient data, wherein the configuration of the breast rest apparatus includes a shape of at least one of a first concavity provided on a top panel or a second concavity provided on a front panel; and a three-dimensional printer configured to produce the breast rest apparatus according to the determined configuration, wherein the breast rest apparatus includes the top panel and the front panel, and the top panel and the front panel are connected by a curved transition.

Aspect 14. The system according to aspect 13, wherein the breast rest apparatus further comprises an open end configured to receive a breast test instrument.

Aspect 15. A mammography imaging system comprising the system according to any of aspects 13-14 and a mammogram imaging device configured to use the breast rest apparatus.

What is claimed is:

1. A system comprising:

a plurality of breast rest apparatuses, each apparatus comprising a top panel and a front panel, wherein the top panel and the front panel are connected by a curved transition, the top panel includes a first concavity, the front panel includes a second concavity, and the breast rest apparatuses differ in a shape of at least one of the first concavity or the second concavity; and a processor configured to receive patient data of a patient and determine one of the plurality of breast rest apparatuses for use with the patient based on the patient data, wherein the patient data includes at least one of patient size data and patient treatment history.

2. The system of claim 1, further comprising a first side panel.

3. The system of claim 1, wherein each breast rest apparatus includes an open end configured to receive a breast test instrument.

4. The system of claim 1, wherein at least one of the breast rest apparatuses includes a carbon material.

5. The system of claim 1, wherein for at least one of the breast rest apparatuses, a shape and/or a size of the first concavity and/or a shape and/or size of the second concavity are based on patient data of a patient, wherein the patient data includes at least one of patient size data and patient treatment history.

6. The system of claim 1, further including a mammogram imaging device.

7. The system of claim 1, further comprising a mammogram imaging device.

8. The system of claim 2, wherein the first side panel and the top panel are joined by a second curved transition.

9. The system of claim 2, further comprising a second side panel.

10. The system of claim 9, wherein the first side panel and the top panel are joined by a second curved transition.

11. A system for producing a breast rest apparatus, comprising:

a processor configured to:

receive patient data of a patient, wherein the patient data includes at least one of patient size data and patient treatment history, and determine a configuration for a breast rest apparatus based on the patient data, wherein the configuration of the breast rest apparatus includes a shape of at least one of a first concavity provided on a top panel or a second concavity provided on a front panel; and a three-dimensional printer configured to produce the breast rest apparatus according to the determined configuration, wherein the breast rest apparatus includes the top panel and the front panel, and the top panel and the front panel are connected by a curved transition.

12. The system of claim 11, wherein the breast rest apparatus further comprises an open end configured to receive a breast test instrument.

13. A mammography imaging system comprising the system of claim 11 and a mammogram imaging device configured to use the breast rest apparatus.

14. A system comprising:

a plurality of breast rest apparatuses, each apparatus comprising a top panel and a front panel, wherein the top panel includes a first concavity, the top panel and the front panel are connected by a curved transition, and the breast rest apparatuses differ in a shape of the first concavity; and a processor configured to receive patient data of a patient and determine one of the plurality of breast rest apparatuses for use with the patient based on the patient data, wherein the patient data includes at least one of patient size data and patient treatment history.

15. The system of claim 14, wherein the front panel of each breast rest apparatus has a second concavity.

16. The system of claim 14, further comprising a first side panel; and wherein the first side panel and the top panel are joined by a second curved transition.

17. The system of claim 14, wherein the breast rest plate of each of the breast rest apparatuses is configured to be removably attached to a mammogram imaging system.

18. A system comprising:

a plurality of detachable breast rest apparatuses, each apparatus comprising a top panel and a front panel, wherein the top panel and the front panel are connected by a curved transition and the top panel includes a first concavity, wherein the top panel and the front panel form an open end configured to interface with an existing breast test instrument, and wherein the detachable breast rest apparatuses differ in a shape of the first concavity; and a processor configured to receive patient data of a patient and determine one of the plurality of detachable breast rest apparatuses for use with the patient based on the patient data, the patient data including at least one of patient size data and patient treatment history.

19. The system of claim 18, wherein the front panel of at least one of the plurality of detachable breast rest apparatuses includes a second concavity.

\* \* \* \* \*